United States Patent
Bar-Shalom et al.

(10) Patent No.: US 11,793,752 B2
(45) Date of Patent: Oct. 24, 2023

(54) AQUEOUS GEL COMPOSITION AND ITS USE

(71) Applicant: University of Copenhagen, Copenhagen (DK)

(72) Inventors: Daniel Bar-Shalom, Kokkedal (DK); Jette Jacobsen, Ølstykke (DK); Kasper Dalby, Odense (DK); Anne Marie Lynge Pedersen, Charlottenlund (DK); Peter Vilmann, Jyllinge (DK)

(73) Assignee: University of Copenhagen, Copenhagen K. (DK)

( * ) Notice: Subject to any disclaimer, the term of this patent is extended or adjusted under 35 U.S.C. 154(b) by 276 days.

(21) Appl. No.: 17/147,957

(22) Filed: Jan. 13, 2021

(65) Prior Publication Data

US 2021/0137834 A1 May 13, 2021

Related U.S. Application Data

(63) Continuation of application No. 15/312,960, filed as application No. PCT/EP2015/061282 on May 21, 2015, now abandoned.

(30) Foreign Application Priority Data

May 22, 2014 (EP) .................................... 14169457

(51) Int. Cl.

| | |
|---|---|
| A61K 9/06 | (2006.01) |
| A61K 47/10 | (2017.01) |
| A61K 47/38 | (2006.01) |
| A61K 9/00 | (2006.01) |
| A61K 31/167 | (2006.01) |
| A61K 31/245 | (2006.01) |
| A61K 31/439 | (2006.01) |
| A61K 31/445 | (2006.01) |
| A61K 31/47 | (2006.01) |
| A61K 45/06 | (2006.01) |

(52) U.S. Cl.
CPC ................ *A61K 9/06* (2013.01); *A61K 9/006* (2013.01); *A61K 9/0034* (2013.01); *A61K 31/167* (2013.01); *A61K 31/245* (2013.01); *A61K 31/439* (2013.01); *A61K 31/445* (2013.01); *A61K 31/47* (2013.01); *A61K 45/06* (2013.01); *A61K 47/10* (2013.01); *A61K 47/38* (2013.01)

(58) Field of Classification Search
CPC .......... A61K 9/06; A61K 9/006; A61K 47/38; A61K 47/10
See application file for complete search history.

(56) References Cited

U.S. PATENT DOCUMENTS

| | | | |
|---|---|---|---|
| 4,740,365 | A | 4/1988 | Yukimatsu et al. |
| 6,133,325 | A | 10/2000 | Schwartz et al. |
| 2005/0226822 | A1 | 10/2005 | Garbers et al. |
| 2005/0244521 | A1 | 11/2005 | Strickland et al. |

FOREIGN PATENT DOCUMENTS

| | | |
|---|---|---|
| EP | 0613684 | 9/1994 |
| WO | WO9203124 | 3/1992 |
| WO | WO9209256 | 6/1992 |
| WO | WO02087519 | 11/2002 |
| WO | WO2006028578 | 3/2006 |
| WO | WO2006124219 | 11/2006 |

OTHER PUBLICATIONS

Tsibouklis et al., "Review Article: Toward mucoadhesive hydrogel formulations for the management of xerostomia: The physicochemical, biological, and pharmacological considerations" J. Biomedical Materials Research A, vol. 101A(11), pp. 3327-3338 (Year: 2013).*

* cited by examiner

*Primary Examiner* — Barbara P Badio
(74) *Attorney, Agent, or Firm* — McHale & Slavin, P.A.

(57) ABSTRACT

An aqueous gel composition comprising a) water, at least one polysaccharide and at least one high molecular weight polyethylene oxide, wherein the water content is at least 90% by weight of the composition, and b) a local anaesthetic agent or an analgesic agent, for use as a local anaesthetic or analgesic. The aqueous gel shows transparency, lubricity, stringiness, elongation, extensiveness, and cohesiveness while being devoid of taste and smell and non-tacky or non-sticky.

7 Claims, No Drawings

# AQUEOUS GEL COMPOSITION AND ITS USE

CROSS REFERENCE TO RELATED APPLICATIONS

In accordance with 37 C.F.R. 1.76, a claim of priority is included in an Application Data Sheet filed concurrently herewith. Accordingly, the present invention claims priority as a continuation of U.S. patent application Ser. No. 15/312,960, filed Nov. 21, 2016, which is a § 371 national stage entry of International Application No. PCT/EP2015/061282, filed May 21, 2015, which claims the benefit of the priority of European Patent Application No. 14169457.0, filed May 22, 2014, the entire contents of each are incorporated herein by reference.

FIELD OF THE INVENTION

The present invention relates to an aqueous gel as well as its use. More particularly the present invention relates to an aqueous gel showing transparency, lubricity, stringiness, elongation, extensiveness and cohesiveness while being devoid of taste and smell and not being tacky. The aqueous gel according to the invention may be used as a lubricant, e.g. as carrier for active ingredients such as local anaesthetics, analgesics and other API's and as a carrier for excipients, as a saliva replacement or food lubricant, and as a lubricant on mucosal surfaces, serosal surfaces and skin. Other uses may be submucosal application either for endoscopic mucosal lifting or for carrier of excipients.

BACKGROUND OF THE INVENTION

Hydrophilic polymers are well known in the art as rheology modifiers of aqueous systems. For instance, they are used as thickeners for a wide range of functional systems such as cosmetics, personal care products and medicine.

Local anaesthetics for use in the throat of a patient undergoing direct oro-pharyngeal examination or surgery or endoscopic examination of the upper gastrointestinal tract or respiratory tract are known in the dosage forms of sprays or viscous gels. However, the known products have a number of drawbacks. Thus, these products are mostly disliked by patients as they have an offending taste and numb, besides the intended site, the tongue and parts of the buccal cavity. A spray, while usually applied with a long nozzle directly to the throat, is transported as aerosol by the breathing to the oral cavity. A gel, usually applied with a spoon may spill on the way or regurgitate into the mouth In the case of endoscopy procedures, the gel may interfere with the clarity of the images.

Artificial saliva or saliva substitutes can be used to replace moisture and lubricate in the oral cavity and thereby alleviate oral dryness. These substitutes are available commercially, but they can also be compounded. Artificial salivas are formulated to mimic natural saliva. However, they are often proven to be ineffective for most patients suffering from persistent salivary gland hypofunction and xerostomia (i.e., sensation of dry mouth).

Saliva is important for the maintenance of oral health, and also plays an essential role in a number of oral and gastrointestinal functions. Consequently, patients with reduced salivary secretion and changes in their saliva composition are more susceptible to dental caries, oral infections and mucosal lesions, and often have symptoms of a dry and sore mouth, burning and itching oral mucosa, difficulties in chewing and swallowing dry foods, impaired sense of taste, difficulty in speaking, and problems with acid reflux. These distressing consequences of salivary hypofunction also have a significant negative impact on quality of life and general health status. Several diseases and medical conditions as well as the medications used for treating them, are associated with salivary gland hypofunction (objective evidence of diminished salivary output) and xerostomia (subjective sensation of dry mouth). In autoimmune diseases like Sjögren's syndrome, salivary gland dysfunction is largely related to structural changes in the salivary glands.

Patients who have undergone radiotherapy to cancer in the head and neck region also often have reduced or no saliva production due to destruction of the gland tissue.

Patients with salivary gland hypofunction often add sauces and gravy to foods in large amounts to compensate for the lack of saliva but in the case of salads and fruits which do not readily form a bolus, this does not help, taste becomes a problem and taking artificial saliva can be awkward and embarrassing (as well as ineffective). Further, by changing the taste of the food item, sauces and gravies make it harder to fully appreciate the original taste. These problems with eating can lead to weight loss, nutritional insufficiency, social isolation and impaired quality of life.

Commercially available products come in a variety of formulations including solutions, sprays, gels and lozenges. In general, they contain an agent to increase viscosity, such as carboxymethylcellulose or hydroxyethylcellulose, minerals such as calcium and phosphate ions and fluoride, preservatives such as methyl- or propylparaben, flavourings and related agents. Attempts have been made to include "natural components" of saliva such as hyaluronic acid or mucins but the results have been disappointing and those products are expensive.

Different spray formulations are available, which are meant to be applied directly to the mouth and throat of a patient suffering from salivary gland hypofunction before swallowing a food item. Alternatively (or alongside), the patient liquefies the food in a blender or food processor.

The use of these formulations is associated with social stigmatization, as it will be obvious for everyone that the patient is struggling with the intake of food.

U.S. Pat. No. 4,740,365 discloses a sustained-release preparation used for mucous membranes in the oral cavity.

U.S. Pat. No. 5,068,225 relates to a viscoelastic fluid for use in surgery and other therapies and method of using same.

U.S. Pat. No. 6,133,325 relates to bioresorbable compositions of carboxypolysaccharide polyether intermacromolecular complexes and methods for their use in reducing surgical adhesions.

U.S. Pat. No. 8,823,334 relates to a topical anesthetic containing about 3 wt % to 10 wt % tetracaine in a vehicle suitable for administration to the mucosa.

WO 92/03124 discloses a polymeric complex composition comprising a reaction complex formed from a polycarbophil and alginic acid.

WO 92/09256 relates to a water-based human tissue lubricant.

WO 02/087519 relates to shaving compositions containing highly lubricious water soluble polymers.

US 2005/0226822 relates to oral care products containing ovomucin.

US2005/0244521 discloses a tobacco composition comprising tobacco and a "format", wherein said composition is readily disintegrable in the mouth, and wherein said format may comprise a polymer.`

WO 2006/028578 discloses use of polyethylene glycol based fluidized polymer suspension in functional systems.

WO 2006/124219 discloses a shaving composition comprising water, a water dispersible surface active agent, a lubricious water soluble polymer, water insoluble particles, and a hydrogel-forming polymer.

EP 0 613 684 relates to a solid form product for alleviating xerostomia.

There is, however, a need for a lubricant for mucosal membranes, serosal surfaces and for submucosal applications in the form of a gel which exhibits stringiness and lubricity while not being tacky.

OBJECT OF THE INVENTION

It is an object of embodiments of the invention to provide an aqueous gel composition which acts as a lubricant for mucosal membranes, serosal surfaces or skin, and which exhibits stringiness, lubricity and is non-tacky.

It is a further object of embodiments of the invention to provide a gel composition which fills as many functions of the natural saliva as possible; it lubricates the mouth enabling normal speech, provides a comfortable feeling of hydration, wetting and lubrication, blends efficiently with solid food and lubricates the passage of food through the throat.

It is a further object of embodiments of the invention to provide a gel, which acts as a carrier for active ingredients to the oral cavity and throat such as local anaesthetics, analgesics, anti-inflammatory agents, anti-infective agents such as antifungal, antibacterial, antiviral and anti-parasitic agents, caries preventive agents, and optionally, pH regulating agents, flavouring agents, taste correcting substances, texture modifiers, colourants and preservatives.

It is a further object of embodiments of the invention to provide a gel which is used to lubricate insertion of devices and appliances to other body cavities such as vagina, uterus, rectum, urethra, ear canal, lacrimal duct, nose, sinuses, thoracic and abdominal cavity and oesophagus.

It is a further object of embodiments of the invention to provide an aqueous gel composition which may be used to lift the mucosa by submucosal injection either in order to perform endoscopic submucosal resection/dissection or to function as a carrier of active substances.

SUMMARY OF THE INVENTION

It has been found by the present inventors that, by combining at least one polysaccharide and at least one high molecular weight polyethylene oxide in a composition having a high water content, an aqueous gel composition having a desirable combination of properties is obtained.

So, in a first aspect the present invention relates to an aqueous gel composition comprising:
a) water, at least one polysaccharide and at least one high molecular weight polyethylene oxide, wherein the water content is at least 90% by weight of the composition; and
b) a local anaesthetic agent or an analgesic agent;
for use as a local anaesthetic or analgesic.

In a second aspect the present invention relates to an aqueous gel composition comprising:
a) water, at least one polysaccharide and at least one high molecular weight polyethylene oxide, wherein the water content is at least 90% by weight of the composition; and
b) optionally a caries-preventive agent, an antifungal agent, an antibacterial agent, an antiviral agent, an anti-parasitic agent, a flavouring agent, a taste correcting substance, a texture modifier, a colourant, a pH regulating agent, and a preservative;
for use as a saliva substitute.

In a third aspect the present invention relates to an aqueous gel composition comprising:
a) water, at least one polysaccharide and at least one high molecular weight polyethylene oxide, wherein the water content is at least 90% by weight of the composition; and
b) optionally a caries-preventive agent, an antifungal agent, an antibacterial agent, an antiviral agent, an anti-parasitic agent, a flavouring agent, a taste correcting substance, a texture modifier, a colourant, a pH regulating agent, and a preservative;
for use as a food lubricant.

In a fourth aspect the present invention relates to an aqueous gel composition comprising water, at least one polysaccharide and at least one high molecular weight polyethylene oxide, wherein the water content is above 98% by weight of the composition, more preferably in the range 98.5-99.5% by weight of the composition, such as in the range 98.7-99.3% by weight of the composition.

In a fifth aspect the present invention relates to an aqueous gel composition according to the invention for use as a lubricant for mucosal membranes, serosal surfaces, skin and for submucosal applications.

In a sixth aspect the present invention relates to an aqueous gel composition according to the invention for use as a lubricant for devices and appliances.

DETAILED DISCLOSURE OF THE INVENTION

Definitions

The term "aqueous gel" refers to an aqueous dispersion comprising water and a hydrophilic polymeric substance dispersed therein.

The term "additive" refers to any active ingredient for use in an aqueous gel composition according to the invention. Non-limiting examples thereof include local anaesthetics, analgesics, anti-inflammatory agents, anti-infective agents such as antifungal, antibacterial, antiviral and anti-parasitic drugs, anti-caries agents or caries-preventive agents, and excipients such as pH regulating agents, preservatives, texture modifiers, colourants, flavouring agents and taste correcting substances.

The term "polysaccharide" refers to a polymeric carbohydrate molecule composed of long chains of monosaccharide units bound together by glycosidic linkages.

The term "cellulose" refers to an organic compound with the general formula $(C_6H_{10}O_5)_n$, a polysaccharide consisting of a linear chain of several hundred to over ten thousand β(1→4) linked D-glucose units. A "derivative" of cellulose refers to a cellulose compound, wherein the hydroxyl groups thereof are partially or fully reacted with various substituents.

The terms "polyethylene oxide" (PEO) and polyoxyethylene (POE) refer to a polyether compound of the general formula $H-(O-CH_2-CH_2)_n-OH$. Polyethylene glycol (PEG) has the same structure as PEO/POE but the starting monomers ethylene oxide and ethylene glycol respectively and the synthesis methods used are different.

The term "saliva substitute" refers to a substance used to substitute the saliva in patients having a dry mouth or xerostomia.

The term "food lubricant" refers to a preparation which, when added to food prior to insertion into the mouth will, upon mastication enable the formation of an easily swallowable bolus.

The terms "lubricancy" and "lubricity", which in the present context are used interchangeably, refers to the property of a composition to lubricate, i.e. make slippery, smooth and lessen friction.

Specific Embodiments of the Invention

In an embodiment of the invention the water content of the aqueous gel composition is at least 95% by weight of the composition, more preferably at least 97% by weight of the composition. Thereby a gel having highly desirable properties in terms of stringiness, lubricity and cohesiveness may be obtained.

In an embodiment of the invention the water content is above 98% by weight of the composition, more preferably in the range 98.5-99.5% by weight of the composition, such as in the range 98.7-99.3% by weight of the composition.

In an embodiment of the invention the at least one polysaccharide is selected from the group consisting of cellulose and derivatives thereof, optionally substituted alkylcelluloses, gums, pectin, carrageenan and alginates.

In an embodiment of the invention the at least one cellulose and derivatives thereof, optionally substituted alkylcelluloses, gums, pectin and carrageenan is selected from the group consisting of methylcellulose, carboxymethylcellulose, hydroxyethylcellulose, hydroxypropylcellulose, hydroxypropylmethylcellulose, xanthan gum, tara gum, guar gum, arabic (Acacia) gum, gellan gum, pullulan gum, cassia gum, carob gum, carregeenan, pectin, locust bean gum, welan gum, konjac, and karaya.

In an embodiment of the invention the methylcellulose, carboxy-methylcellulose, hydroxyethylcellulose, hydroxypropylcellulose, hydroxypropylmethylcellulose, xanthan gum, tara gum, guar gum, arabic (Acacia) gum, gellan gum, pullulan gum, cassia gum, carob gum, carregeenan, pectin, locust bean gum, welan gum, konjac, and karaya is preferably selected from the group consisting of methylcellulose, carboxy-methylcellulose, hydroxypropylmethylcellulose, xanthan gum, and guar gum, more preferably methylcellulose, hydroxypropyl methylcellulose, carboxymethylcellulose, gellan gum or xanthan gum. The above polysaccharides are devoid of any taste and smell and are available at low cost.

In an embodiment of the invention the at least one polysaccharide is a methylcellulose or a hydroxypropylmethyl cellulose and is preferably hydroxypropylmethyl cellulose (HPMC). Methylcellulose and hydroxypropyl methylcellulose are available commercially under the trade name METHOCEL™ as a line of cellulose ether products produced by The Dow Chemical Company. The initial letter identifies the type of cellulose ether. An "A" identifies methylcellulose products and "E", "F", "K", "J" and "310-series" identify different hydroxypropyl methylcelluloses.

In an embodiment of the invention the at least one high molecular weight polyethylene oxide is of a molecular weight of at least 200,000, preferably of a molecular weight of at least 600,000, preferably of a molecular weight of at least 1,000,000, such as in the range 1,000,000 to 7,000,000, more preferably of a molecular weight in the range 1,000,000-6,000,000, such as of a molecular weight in the range 1,000,000 to 5,000,000, such as of a molecular weight in the range 1,000,000 to 4,000,000. Polyethylene oxide polymers are available commercially under the trade name of POLYOX™ followed by a subscript indicating its type. Thus e.g. POLYOX™ 301 refers to a PEO having a molecular weight of approximately 4,000,000, whereas POLYOX™ 303 refers to a PEO having a molecular weight of approximately 7,000,000.

In an embodiment of the invention the content of the at least one polysaccharide is in the range 0.1-3% by weight of the composition, more preferably in the range 0.3-2.0% by weight of the composition, such as in the range 0.4-1.5% by weight of the composition, more preferably in the range 0.5-1.5% by weight of the composition, such as about 0.6-1.2% by weight of the composition, such as about 0.8% by weight of the composition.

In an embodiment of the invention the content of the at least one high molecular weight polyethylene oxide is in the range 0.05-2% by weight of the composition, more preferably in the range 0.1-1% by weight of the composition, more preferably in the range 0.1-0.5% by weight of the composition, such as about 0.3% by weight of the composition.

In an embodiment of the invention the content of the at least one polysaccharide in the composition is in the range 0.5-1.5% by weight of the composition, preferably in the range 0.6-1.2% by weight of the composition, such as about 0.8% by weight of the composition, and the content of the at least one high molecular weight polyethylene oxide in the composition is in the range 0.1-1% by weight of the composition, preferably in the range 0.1-0.5% by weight of the composition, such as about 0.3% by weight of the composition.

In an embodiment of the invention the aqueous gel composition according to the invention comprises a local anaesthetic agent or analgesic agent selected from procaine, amethocaine, cocaine, lidocaine (also known as Lignocaine), prilocaine, bupivacaine, levobupivacaine, ropivacaine, mepivacaine, dibucaine, benzocaine, tetracaine, etidiocine, and ropivacaine. It is to be understood, however, that the above list is non-exhaustive and that other local anaesthetic agents or analgesic agents may be used in a particular aqueous gel composition according to the invention.

In an embodiment of the invention the aqueous gel composition further comprises at least one additive. Non-limiting examples thereof include additives selected from the group consisting of a flavouring agent, a taste correcting substance, a texture modifier (such as one or more lipids), a colourant, a pH regulating agent, a preservative, a therapeutically active agent, such as sucralfate, a steroid, a caries-preventive agent (such as e.g. fluoride), an antifungal agent, an antibacterial agent (such as e.g. Lyzozyme, triclosan, metronidazole), an antiviral agent (acyclovir), and an anti-parasitic agent. A person skilled in the art will readily be able to select any suitable additive according to the purpose intended and it is to be understood, that the above list is non-exhaustive and merely illustrate exemplary additives and that other additives may be used singly or in combination in a particular aqueous gel composition according to the invention.

The aqueous gel composition according to the invention may be prepared in a manner known per se. Thus, non-limiting examples of the preparation thereof may be found in Handbook of Pharmaceutical Excipients, fifth ed., Raymond C Rowe et al. and include mixing of the polymers with ice-cold water under vigorous agitation; wetting the polymers with a portion of hot, 65-85° C., water and then adding, under agitation, the rest of the water as ice or ice-water; or the polymers may be moistened with an organic solvent such as ethanol prior to the addition of water.

In an embodiment of the invention the aqueous gel composition comprises an active ingredient for the treatment of oral mucosal conditions/diseases such as lichen planus, candidiasis, angular cheilitis, recurrent aphthous stomatitis, recurrent herpes labialis, glossitis/stomatitis migrans, discoid lupus lesions, burning mouth syndrome, burning mouth syndrome, mucositis a.o.

In another embodiment, it might be used as eye lubricant and as carrier of active substances to the eyes.

Further, it may be used as lubricant in massage and sexual activities.

In another embodiment, it might be used as a carrier of active substances to the vagina, urethra, uterus, nose, sinus, throat, ears, or rectum or any other mucosal or serosal tissue or skin.

Finally it might be useful in lubricating skin to skin friction, devices-skin friction, such as with prosthetic devices, and friction of device parts such as endoscope against sleeves and mouth-guards and intra-device friction such as wires in an endoscope.

Example 1

A number of aqueous gel compositions were prepared by adding the pre-weighted and premixed polymers to the water at low temperature (under 3° C.) while agitating the water with an Electrolux Stick Mixer ES™ 6200 at highest speed. The agitation was maintained until no more dry particles or lumps could be seen.

The quality of the individual gel compositions appears from the below table I.

TABLE I

| Material 1 (M1) | Material 2 (M2) | Molecular structure material 1 | Molecular structure material 2 | Quality of gel | Comment | Conc. (M1 %, M2 %) |
| --- | --- | --- | --- | --- | --- | --- |
| Methocel K250M (HPMC) | Polyox 301 | [HPMC structure] | [PEG structure] | —<br>+<br>++<br>+++<br>+++ | | 0,03/0,3<br>0,1/0,3<br>0,3/0,3<br>0,8/0,3<br>1,0/0,3 |
| Methocel K250M (HPMC) | — | [HPMC structure] | — | +<br>++<br>++ | No stringiness (all conc.) | 0.6<br>0.8<br>1.0 |
| Polyox 301 | — | [PEG structure] | — | — | Water like with stringiness | 0.3 |
| Methocel K250M (HPMC) | Polyox N60K | [HPMC structure] | [PEG structure] | ++ | Thin | 0,8/1,5 |

TABLE I-continued
| Material 1 (M1) | Material 2 (M2) | Molecular structure material 1 | Molecular structure material 2 | Quality of gel | Comment | Conc. (M1 %, M2 %) |
|---|---|---|---|---|---|---|
| Methocel K250M (HPMC) | Polyox N12K | 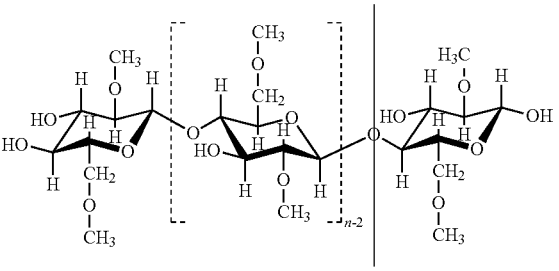 | 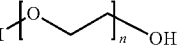 | ++ | Thin | 0,8/0,75 |
| Maize starch | — | 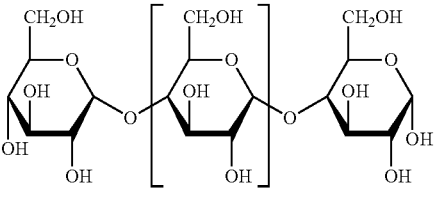 | — | — | Jelly | 10 |
| Maize starch | Polyox 301 | 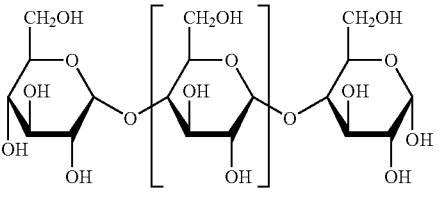 | 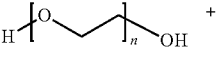 | + | Jelly/gel | 5/0,3 |
| CMC 40.000 | Polyox 301 | 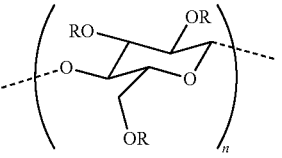<br>R = H or $CH_2CO_2H$ | 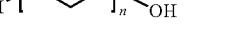 | +++ | | 0,8/0,3 |
| Kelcogel (gellan gum) | Polyox 301 | 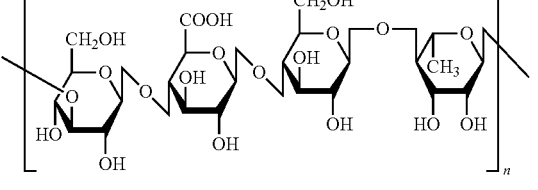 | 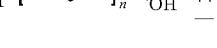 | ++<br>++<br>— | Jelly | 0,1/0,3<br>0,2/0,3<br>0,8/0,3 |
| Methocel K15M (HPMC) | Polyox 301 | 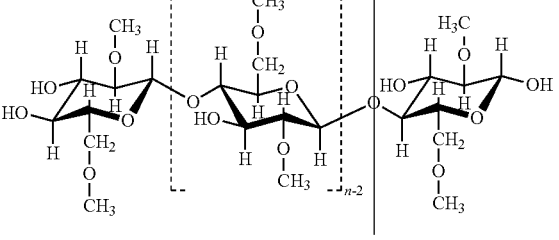 | 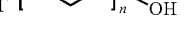 | ++ | | 0.8/0.3 |

TABLE I-continued

| Material 1 (M1) | Material 2 (M2) | Molecular structure material 1 | Molecular structure material 2 | Quality of gel | Comment | Conc. (M1 %, M2 %) |
|---|---|---|---|---|---|---|
| Keltrol (xanthan gum) | Polyox 301 | [xanthan gum structure] | $H\!\!-\!\!\left[O\!\!-\!\!\diagdown\!\!\diagup\right]_n\!\!OH$ | — | Jelly | 0.7/0.3 |
| Methylcellulose SGA | — | [methylcellulose structure] R = H or CH$_3$ | — | — + | Very thin | 2 5 |
| Methylcellulose SGA | Polyox 301 | [methylcellulose structure] R = H or CH$_3$ | $H\!\!-\!\!\left[O\!\!-\!\!\diagdown\!\!\diagup\right]_n\!\!OH$ | +(+) | | 5/0.3 |
| Methocel A40M (MC) | Polyox 301 | [HPMC structure] | $H\!\!-\!\!\left[O\!\!-\!\!\diagdown\!\!\diagup\right]_n\!\!OH$ | + | A thin gel | 0.8/0.3 |
| Methocel fast hydrating K100M (HPMC) | Polyox 301 | [HPMC structure] | $H\!\!-\!\!\left[O\!\!-\!\!\diagdown\!\!\diagup\right]_n\!\!OH$ | ++ | | 0.8/0.3 |

TABLE I-continued

| Material 1 (M1) | Material 2 (M2) | Molecular structure material 1 | Molecular structure material 2 | Quality of gel | Comment | Conc. (M1 %, M2 %) |
|---|---|---|---|---|---|---|
| Methocel K4M (HPMC) | Polyox 301 | [structure] | [structure] | + | | 0.8/0.3 |
| Methocel K4M (HPMC) | — | [structure] | — | — | | 0.8 |
| Methocel F4M (HPMC) | Polyox 301 | [structure] | [structure] | — | | 0.8/0.3 |
| Methocel F4M (HPMC) | — | [structure] | — | — | | 0.8 |
| Methocel E4M (HPMC) | Polyox 301 | [structure] | [structure] | + | | 0.8/0.3 |

TABLE I-continued

| Material 1 (M1) | Material 2 (M2) | Molecular structure material 1 | Molecular structure material 2 | Quality of gel | Comment | Conc. (M1 %, M2 %) |
|---|---|---|---|---|---|---|
| Methocel E4M (HPMC) | — | 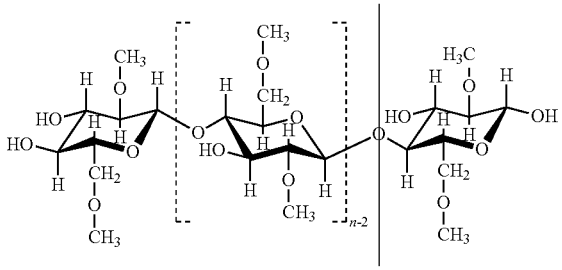 | — | — | — | 0.8 |
| Methocel A4M (MC) | Polyox 301 | 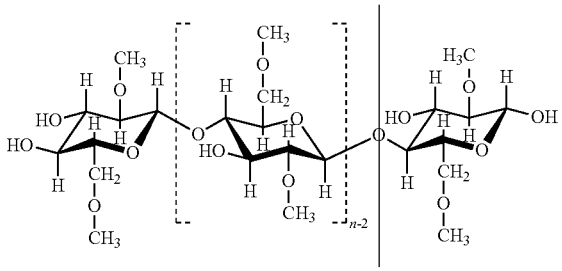 | 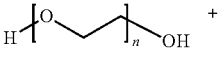 | + | | 0.8/0.3 |
| Methocel A4M (MC) | — | 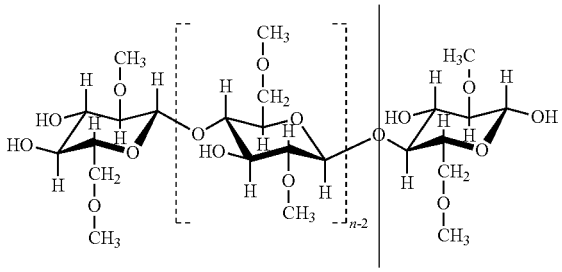 | — | — | | 0.8 |
| Arabic gum | — | | | +(+) | — | |
| Arabic gum | Polyox 301 | | 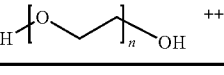 | ++ | — | |

Example 2

An aqueous vehicle having the following composition:
0.2% by weight of polyethylene oxide (Polyox WSR 301)
0.5% by weight of HPMC (Methocel K250M)
q.s. water
was prepared by adding the polyethylene oxide and HPMC to ice-cold water while agitating the mixture with an Electrolux Stick Mixer ES™ 6200 at highest speed. The agitation was maintained until no more dry particles or lumps could be seen. Sucralfate in an amount of 5.3% by weight of the above vehicle was added under stirring to obtain a sucralfate-containing gel composition.

The sucralfate-containing gel composition was administered to patients with xerostomia also having inflammatory mucosal lesions twice daily at a dose of one spoonful per dose. Significant symptom relief was observed after a few days of treatment.

LIST OF REFERENCES

U.S. Pat. No. 4,740,365
U.S. Pat. No. 5,068,225
U.S. Pat. No. 6,133,325
U.S. Pat. No. 8,623,334
WO 92/03124
WO 92/09256
WO 02/087519
US 2005/0226822
US 2005/0244521
WO 2006/028578
WO 2006/124219
EP 0 613 684

The invention claimed is:

1. A method of substituting natural produced saliva with a saliva substitute composition comprising:
providing to a person in need of a saliva substitute an orally administered saliva substitute composition comprising: water, at least one polysaccharide and at least one high molecular weight polyethylene oxide, wherein the water content is at least 90% by weight of the composition; the at least one high molecular weight polyethylene oxide is of a molecular weight in the range of 1,000,000-7,000,000, the content of the at least one polysaccharide in the composition is in the range 0.5-1.5% by weight of the composition, and the content of the at least one high molecular weight polyethylene oxide in the composition is in the range 0.1-1% by weight of the composition.

2. The method of substituting natural produced saliva with a saliva substitute composition according to claim 1, wherein the at least one polysaccharide is selected from the group consisting of cellulose and derivatives thereof, optionally substituted alkylcelluloses, gums, pectin, carrageenan and alginates.

3. The method of substituting natural produced saliva with a saliva substitute composition according to claim 1, wherein said saliva substitute composition further comprises at least one therapeutically active agent.

4. The method of substituting natural produced saliva with a saliva substitute composition according to claim 3, wherein said therapeutically active agent is a local anaesthetic agent, or an analgesic agent.

5. The method of substituting natural produced saliva with a saliva substitute composition according to claim 3, wherein said therapeutically active agent is an anti-infective agent.

6. The method of substituting natural produced saliva with a saliva substitute composition according to claim 5, wherein said anti-infective agent is selected from the group consisting of an antifungal agent, an antibacterial agent, an antiviral agent, and an anti-parasitic agent.

7. The method of substituting natural produced saliva with a saliva substitute composition according to claim 1, wherein said saliva substitute composition further comprises an additive selected from any one or more of members of the group consisting of a caries-preventive agent, a texture modifier, a colorant, a pH regulating agent, and a preservative.

* * * * *